United States Patent [19]
Long et al.

[11] Patent Number: 5,633,133
[45] Date of Patent: May 27, 1997

[54] LIGATION WITH HAMMERHEAD RIBOZYMES

[76] Inventors: David M. Long; Olke C. Uhlenbeck, both of Department of Chemistry & Biochemistry, University of Colorado, Campus Box 215, Boulder, Colo. 80309-0215; Klemens J. Hertel, 70 Canal St., Medford, Mass. 02155

[21] Appl. No.: 275,156

[22] Filed: Jul. 14, 1994

[51] Int. Cl.$^6$ .................... C12Q 1/68; C12N 15/11; C07H 21/04

[52] U.S. Cl. .................... 435/6; 435/91.31; 435/172.1; 435/172.3; 536/23.1; 536/23.2

[58] Field of Search .................... 435/6, 91.31, 172.1, 435/172.3, 320.1, 240.1; 536/23.1, 23.2, 24.5; 514/44

[56] References Cited

FOREIGN PATENT DOCUMENTS

| | | |
|---|---|---|
| 9103162 | 3/1991 | WIPO . |
| 9207065 | 4/1992 | WIPO . |
| 9315187 | 8/1993 | WIPO . |

OTHER PUBLICATIONS

Haseloff et al. Nature 334:585 (1988).
Bartel and Szostak, "Isolation of New Ribozymes From a Large Pool of Random Sequences," *Science* 261:1411–1418 (1993).
Berzal–Herranz et al., "In vitro selection of active hairpin ribozymes by sequential RNA–catalyzed clevage and ligation reactions," *Genes & Development* 6:129–134 (1992).
Berzal–Herranz et al., *EBMO J.* 12:2567–2574 (1993).
Dahm and Uhlenbeck, *Biochemistry* 30:9464–9469 (1991).
Hertel et al., "A Kinetic Thermodynamic Framework for the Hammerhead Ribozyme Reaction," *Biochemistry* 33:3374–3385 (1994).
Izatt et al., "Sites and Thermodynamic Quantities Associated with Proton and Metal Ion Interaction with Ribonucleic Acid, Deoxyribonucleic Acid, and Their Constituent Bases, Nucleosides and Nucleotides," *Chem. Rev.* 71:439–481 (1971).
Joyce, "Directed Molecular Evolution," *Scientific American* 267:90–97 (1992).
Koizumi and Ohtsuka, *Biochemistry* 30:5145–5150 (1991).
Perreault et al., "Mixed Deoxyribo–and Ribo–Oligonucleotides with Catalytic Activity," *Nature* 344:565–567 (1990).
Pieken et al., "Kinetic Characterization of Ribonuclease–Resistant 2'–Modified Hammerhead Ribozymes," *Science* 253:314–317 (1991).
Rossi et al, "Ribozymes as Anti–HIV–1 Therapeutic Agents: Principles, Applications, and Problems," *Aids Research and Human Retroviruses* 8:183 (1992).
Usman and Cedergren, "Exploiting the chemical synthesis of RNA," *TIBS* 17:334–339 (1992).

*Primary Examiner*—John L. LeGuyader
*Attorney, Agent, or Firm*—Lyon & Lyon

[57] ABSTRACT

The claimed invention is drawn to a method for ligation of an enzymatic nucleic acid molecule having a hammerhead motif to a separate nucleic acid molecule. The method includes use of ligation enhancing conditions in which ligation is enhanced at least two fold over that observed in a medium containing only $Mg^{2+}$ as a divalent cation at 20° C.

15 Claims, 6 Drawing Sheets

LIGATION WITH HAMMERHEAD RIBOZYMES

BACKGROUND OF THE INVENTION

This invention relates to methods for ligating RNA molecules together and to improved ribozymes.

Berzal-Herranz et al, 6 *Genes & Development* 129, 132, 1992, describes in vitro selection of active hairpin ribozymes by use of cleavage and ligation reactions. It indicates that the authors "expect that an analogous selection method could be developed for other small transacting ribozymes, for example, the hammerhead ribozyme, if conditions favoring a ligation reaction can be identified."

SUMMARY OF THE INVENTION

A ribozyme is an enzymatic nucleic acid (e.g., RNA) molecule that can cleave and/or ligate either to a part of itself or to other separate RNA or even DNA molecules. There are several different ribozyme motifs and all have potential usefulness as therapeutic agents to down regulate expression of unwanted RNAs in cells. Each ribozyme motif has its own strengths and weaknesses as a therapeutic agent. The ideal ribozyme is likely to be one that: (i) has the potential to target many different sites on the target RNA, (ii) can operate under a wide variety of reaction conditions, (iii) is small, so that it can be synthesized cheaply and delivered exogenously to cells, and (iv) is well understood, so that design of new ribozymes targeted to new sites is relatively simple. The hammerhead ribozyme comes closest to this ideal in that it is small (usually 30–40 nucleotides, nt), has the potential to be targeted against any UH sequence (U followed by anything but G) in the target RNA, and is well studied and well understood. However, in a typical reaction, the hammerhead ribozyme lacks one feature that is available and useful to other ribozymes—it lacks the ability to reverse the cleavage reaction to any great extent.

Any ribozyme that can cleave RNA also has the potential to put the RNAs back together by simply reversing the cleavage reaction. How efficiently the reverse reaction works depends upon the ribozyme, the target RNA and the reaction conditions. The group I intron ribozymes and the hairpin ribozymes can reverse the cleavage reaction very efficiently to yield greater than 50% ligated RNAs under favorable conditions. In contrast, previous published attempts to reverse the cleavage reaction with the hammerhead ribozyme indicate yields of less than 2% ligated products (Hertel, K. J., Herschlag, D. and Uhlenbeck, O. C. (1994) *Biochemistry* 33, 3374–3385). Both the group I intron ribozymes and the hairpin ribozymes are thought to promote the ligation reactions by forming secondary and tertiary interactions that hold in place the two reacting RNAs. The low yield of ligated products from the hammerhead ribozyme may be the result of a high entropic cost of bringing the two reacting RNAs close together, which, in turn, may be due to the lack of tertiary interactions within the hammerhead core (see FIG. 1).

Reverse cleavage is a useful feature of the group I introns and the hairpin ribozymes. The ligation reaction can be designed so that the ribozyme becomes covalently attached to the ligated RNA rather than to a separate acceptor RNA. This provides a tag which allows one to identify which ribozyme was able to react with which site on the target RNA. Through PCR amplification, a small number of ligated ribozyme/target combinations can be isolated and sequenced from a larger pool of reactants. This approach has been used with the group I introns to select for modified ribozymes capable of performing a number of reactions (for a review see Joyce, G. F. (1992) *Scientific American* 267, 90–97; Szostak, J. W. (1993) *TIBS* 17, 89–93). The approach has also been successfully employed on the hairpin ribozymes to identify the nucleotide sequences necessary for hairpin ribozyme activity (Berzal-Herranz et al. supra; Berzal-Herranz et al. (1993) *EMBO J.* 12, 2567–2574).

Applicant now provides for the first time environmental conditions that shift the cleavage/ligation equilibrium strongly towards ligated RNA and makes it possible to employ, with the hammerhead motifs, similar selection strategies to those discussed above for other ribozyme motifs. More importantly, it allows accessible target sites to be identified through ligation of the ribozyme to its target. Thus, it allows selection in vivo or in vitro for therapeutically useful ribozymes, or for ribozymes which can indicate therapeutically useful targets.

Thus, applicant is the first to allow use of hammerhead ribozymes in a selection procedure in which ligation activity is used, rather than cleavage activity, to select for active ribozymes. Specifically, applicant has determined that specific cations (in particular, divalent cations such as manganese and cobalt) provide significantly better ligation results than with the commonly provided magnesium ions. In addition, applicant has determined that low temperatures favor the ligation reaction, for example, at temperatures between 2° C. and 10° C. From these results those in the art will recognize that conditions now exist for useful in vitro selection of active hammerhead ribozymes by sequential RNA catalyzed cleavage and ligation reactions by the protocols described by Berzel-Herranz, supra. Such selected hammerhead ribozymes are useful for design of further ribozymes to specific targets for treatment of various diseases or conditions as described by Draper et al., PCT/US93/04020, the whole of which is hereby incorporated by reference herein (including the details of the design of ribozymes, their therapeutic administration, and in vitro uses).

Thus, in a first aspect the invention features a method for ligation of an enzymatic nucleic acid molecule—having a hammerhead motif—to a separate nucleic acid molecule. The method includes contacting the enzymatic molecule with the separate nucleic acid molecule under ligation enhancing conditions. Such conditions will enhance ligation by at least two-fold over that observed in a medium containing magnesium ions as the only divalent cation at 20° C.

By "enzymatic nucleic acid molecule" is meant a nucleic acid molecule which has complementarity (or is otherwise able to bind with) in a substrate binding region to a specified gene target, and also has an enzymatic activity which is active to specifically cleave or ligate nucleic acid in that target. That is, the enzymatic nucleic acid molecule is able to intra- or inter-molecularly cleave a nucleic acid molecule and thereby potentially inactivate the function of a target RNA molecule. The complementarity of the enzymatic nucleic acid molecule functions to allow sufficient hybridization of it to the target nucleic acid to allow the cleavage or ligation to occur. One hundred percent complementarity is preferred, but complementarity as low as 50–75% may also be useful in this invention. Such nucleic acid molecules may be formed totally of ribonucleotides or may include modified nucleotides, or even non-nucleotides as known in the art, and may also include other sequences, as described by Draper et al., supra. Other relevant publications include Eckstein et al., International Publication No. WO 92/07065; Perrault et al., *Nature* 1990, 344:565; Pieken et al., *Science* 1991, 253:314; Usman and Cedergren, *Trends in Biochem. Sci.* 1992, 17:334; Usman et al., International Publication No. WO 93/15187; and Rossi et al., International Publication No. WO 91/03162.

In preferred embodiments, the enzymatic nucleic acid molecule is formed in a hammerhead motif. Examples of such hammerhead motifs are described by Rossi et al., 8 *Aids Research and Human Retroviruses* 183, 1992 and Draper et al., supra. The specific motifs in these publications are not limiting in the invention and those skilled in the art will recognize equivalent such motifs. In preferred embodiments, a separate RNA molecule is the target for the hammerhead ribozyme, and is an oligonucleotide of length between 5 and 30 bases, or even greater than 10,000 bases, and the hammerhead motif has an enzymatic activity able to cleave separate RNA molecules as described by Draper et al., supra. In more preferred embodiments, the ligation enhancing conditions include cobalt or manganese ions, e.g., at a low temperature between 2° C. and 5° C. or less than 15° C., such that the enhancement is greater than 5-, preferably greater than 10-, or 30-fold over that observed in the above-stated conditions, and such that at least 10% ligation of the nucleic acid molecule to the separate nucleic acid molecule is observed (preferably at least 20% to 50% ligation is observed).

In a second related aspect, the invention features an enzymatic nucleic acid molecule having a hammerhead motif active to ligate a separate nucleic acid molecule to itself with at least 10% ligation efficiency. By 10% ligation efficiency is meant that in limiting substrate or target and excess ribozyme at least 1 in 10 of the substrate molecules is ligated in vitro to a ribozyme after equilibrium is reached, e.g., after about 60 minutes.

In preferred embodiments, the enzymatic nucleic acid molecule is chemically distinct from a natural hammerhead motif in that it includes a thiophosphate or other non-natural linkage (in the appropriate isomeric form) to enhance ligation; or the enzymatic nucleic acid molecule is selected (e.g., as described by Berzal-Herranz et al., supra) to find an enzymatic molecule having significantly increased ligation activity.

In another related aspect, the invention features a method for selection of an enzymatic nucleic acid molecule having a hammerhead motif by in vitro selection under ligation enhancing condition in which ligation is enhanced at least two-fold over that observed in a medium containing magnesium ions as the only divalent cation at about 20° C. In a related aspect, the invention also features a method for screening for a cleavage site by use of an enzymatic nucleic acid molecule having a hammerhead motif with a ligation activity of at least 10% (as defined above) by screening for sites in a potential target molecule which are active in ligation assays either in vivo or in vitro.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of a hammerhead ribozyme and ligation reaction. The ligation reaction involves a self-cleaving RNA ("RZ/P1") that can be mixed with a small oligo ("P2") under the desired conditions and, after equilibrium is reached, assessed for extent of ligation. Cleavage proceeds from left to right in this figure, while ligation proceeds from right to left. The ">P" at the 3' end of RZ/P1 represents a 2' 3'-cyclic phosphate end.

Figure 5:
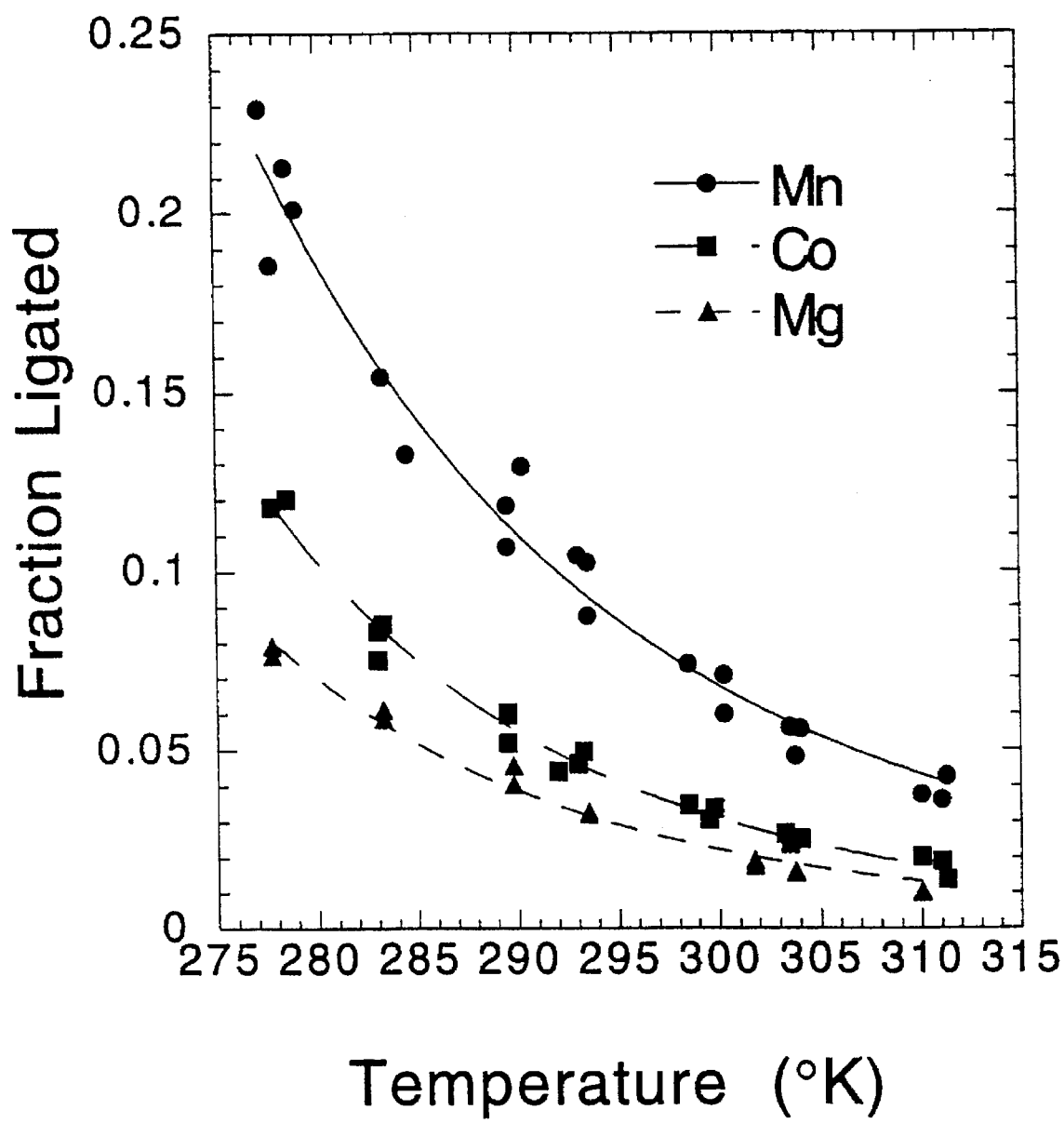

FIG. 5 shows the effect of temperature and metal ion on the extent of ligation. The fraction of ligated RNA was measured as a function of temperature in the presence of three metal ions. Reactions in the presence of 10 mM $Mn^{2+}$ promotes almost 25% ligated RNA at 277° K. (5° C.). It is likely that the hammerhead will ligate to more than 50% at low temperature and high manganese concentration. The entropies and enthalpies of the reactions are very metal ion dependent and indicate that the fraction of ligated RNA is not an intrinsic property of the RNA alone. In fact the affinity of metal ions to RNA appears to be directly related to the ligation efficiency—the tighter the metal binding to the RNA, the greater is the ligation efficiency ($Mn^{2+}$ has a relatively high affinity towards RNA). There are several other divalent metal ions that bind to RNA tightly and are expected now by applicant to be the most effective cofactors for ligation—$Cd^{2+}$, $Zn^{2+}$, $Cu^{2+}$, $Ni^{2+}$ (Izatt, R. M., et al. (1971) *Chem. Rev.* 71, 439–450).

Figure 6:
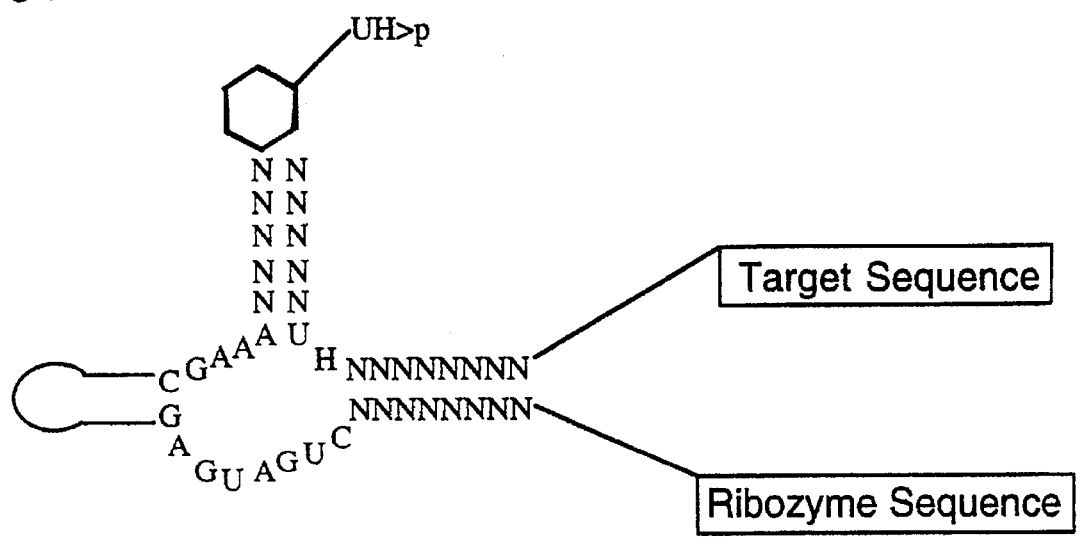
Figure 6:
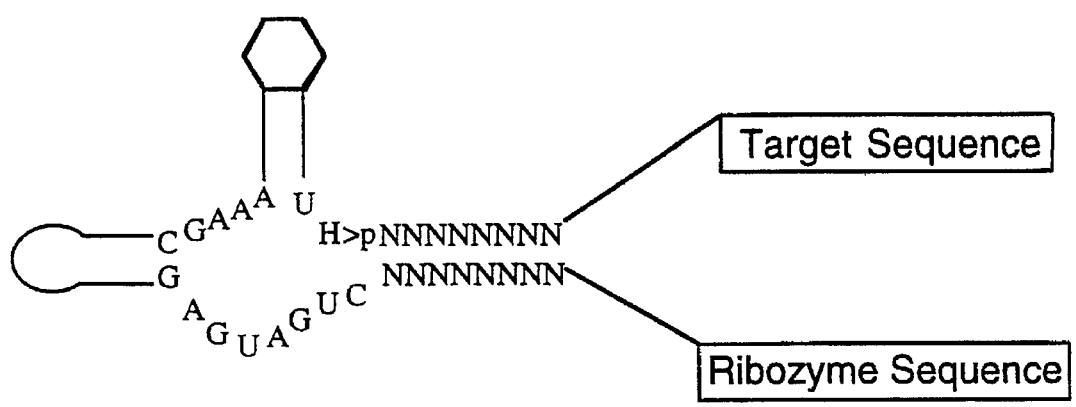
Figure 7:
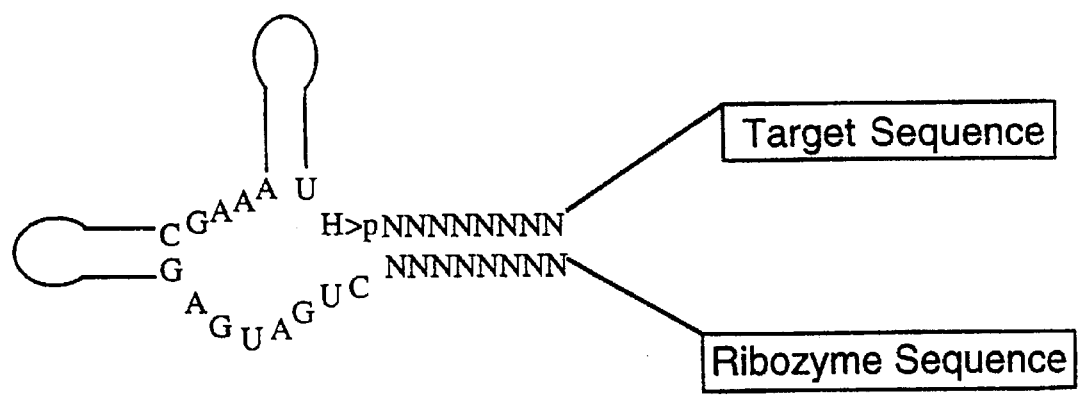

FIGS. 6 and 7 are diagrammatic representations of methods for selection of hammerhead ribozymes with greater ligation efficiencies, using essentially the method described in Berzal-Herranz et al. supra. Although, the figures indicate sequences within the conserved core of a hammerhead ribozyme, it must be noted that the identity of these sequences can vary based on the selection strategy used. For example, the entire core sequence can be randomized and molecules capable of catalyzing efficient ligation reaction can be selected (this strategy is similar to Bartel and Szostak, (1993) Isolation of new ribozymes from a large pool of random sequences. *Science* 261; 1411–1418). Therefore the hammerhead ribozyme core sequence is listed for simplicity, and is not meant to be limiting. (Each N is independently any base, or a non-nucleotide, and may base pair as shown in the figure.)

EXAMPLES

Below are provided examples of methods to enhance ligation reactions for a hammerhead ribozyme. These examples are not limiting, and those in the art will now observe that other equivalent conditions can be determined. These examples show that ligation of hammerhead ribozymes can be enhanced and thus that other conditions can be developed by routine experimentation. In addition, the existence of such conditions now allows selection of highly efficient hammerhead ribozymes able to ligate as described by Berzal-Herranz, supra. Thus, this invention features such selection procedures and the resulting hammerhead ribozymes produced.

The approach herein has been to use a self-cleaving RNA (FIG. 1) that can be mixed with a small oligo ("P2") under the desired conditions and, after equilibrium is reached, assessed for extent of ligation. One such experiment is shown in FIG. 2 where the extent of ligation (S/P) is measured as a function of metal ion concentration at 25° C.

A typical ligation reaction is carried out at 25° C. in the presence of 100 mM PIPES buffer (pH 6.5), 500 nM P2, trace amount of internally labeled RZ/P1 (see FIG. 1) and varying metal ion concentration. The reaction mixture is incubated from 15 min up to 24 h, depending on the concentration and the identity of metal ions.

Figure 1:
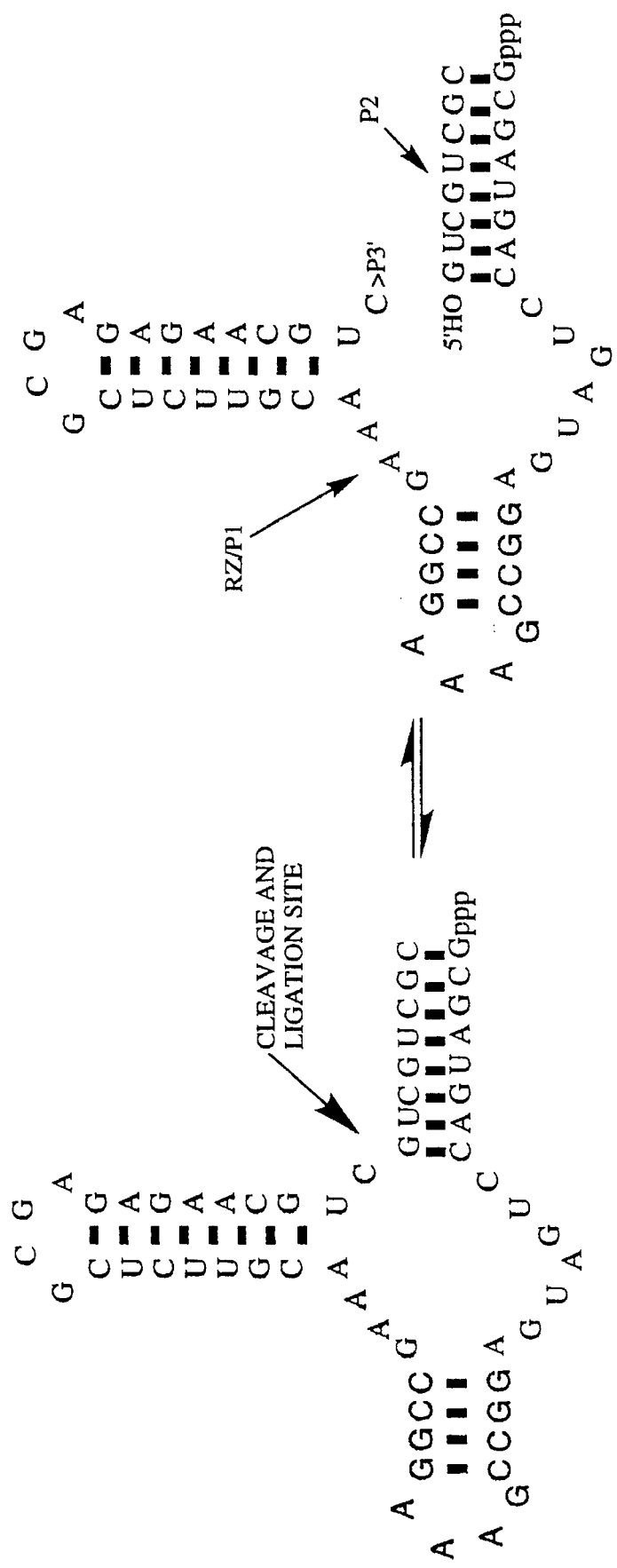
Figure 2:
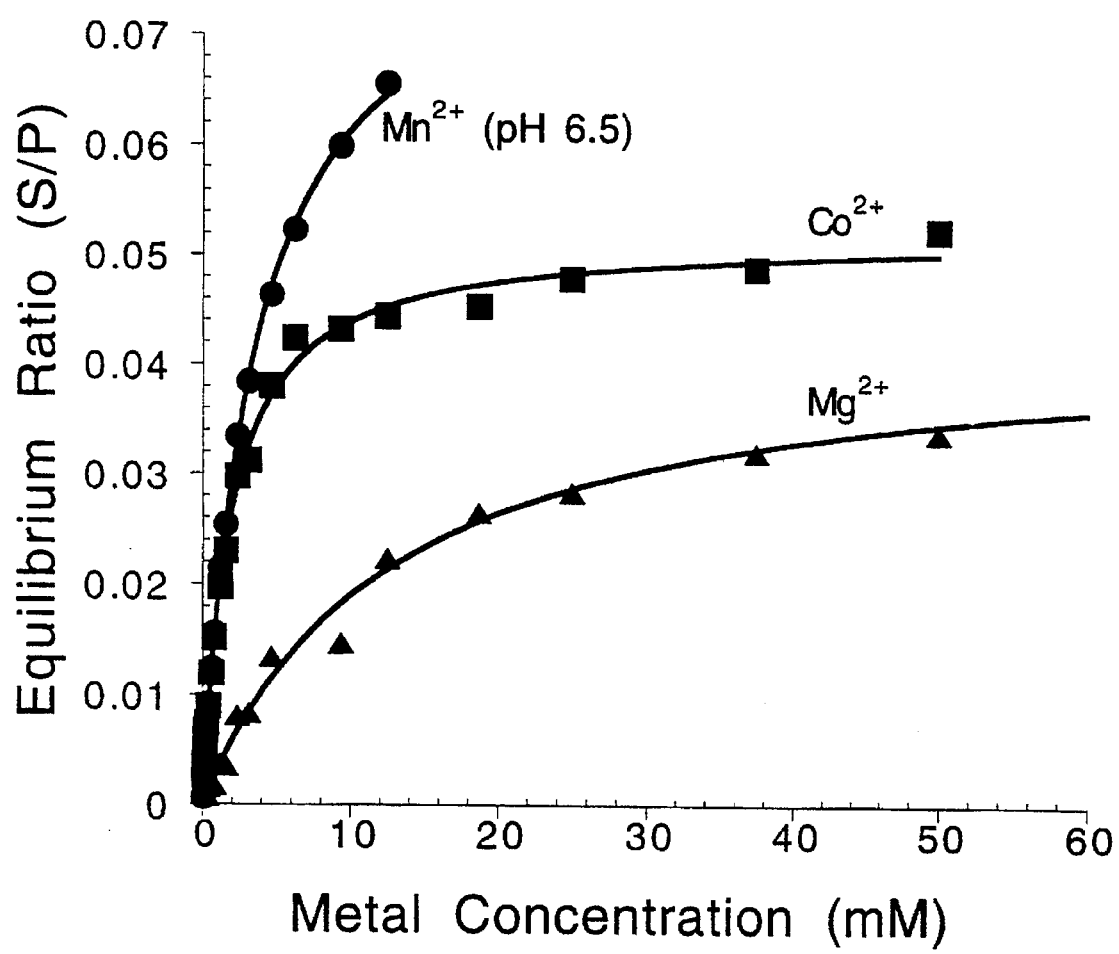
FIG. 2 is a graph showing the effect of metal ion concentration on extent of ligation [Equilibrium Ratio S/P (substrate/product)] at 25° C. for three different divalent cations. $Mn^{2+}$ shows the greatest promotion of ligated products. The metal ion dependence is hyperbolic and has the general form of a binding curve.

Referring to the Figures, FIG. 1 demonstrates that S/P is dependent on the concentration and identity of the metal ion cofactor. In addition, the metal ion dependence of S/P is hyperbolic and has the general form of a binding curve.

Table 1 shows measured apparent dissociation constants (called "Kp") and maximal extents of ligation for different metal ions.

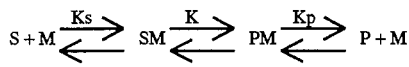

Where,
S=substrate RNA
M=Metal ion
P=Product RNA

TABLE 1

| Parameters that Describe the Metal Ion Concentration Dependence of the Hammerhead Cleavage/Ligation Reaction | | | | |
|---|---|---|---|---|
| Metal Ion | K | Kp (mM) | n | Ks (mM) |
| $Mn^{2+}$ | 12.0 | 4.0 | 0.98 | <0.8 |
| $Co^{2+}$ | 19.2 | 2.2 | 0.97 | <0.45 |
| $Mg^{2+}$ | 23.3 | 13.3 | 1.0 | <2.7 |

Figure 3:
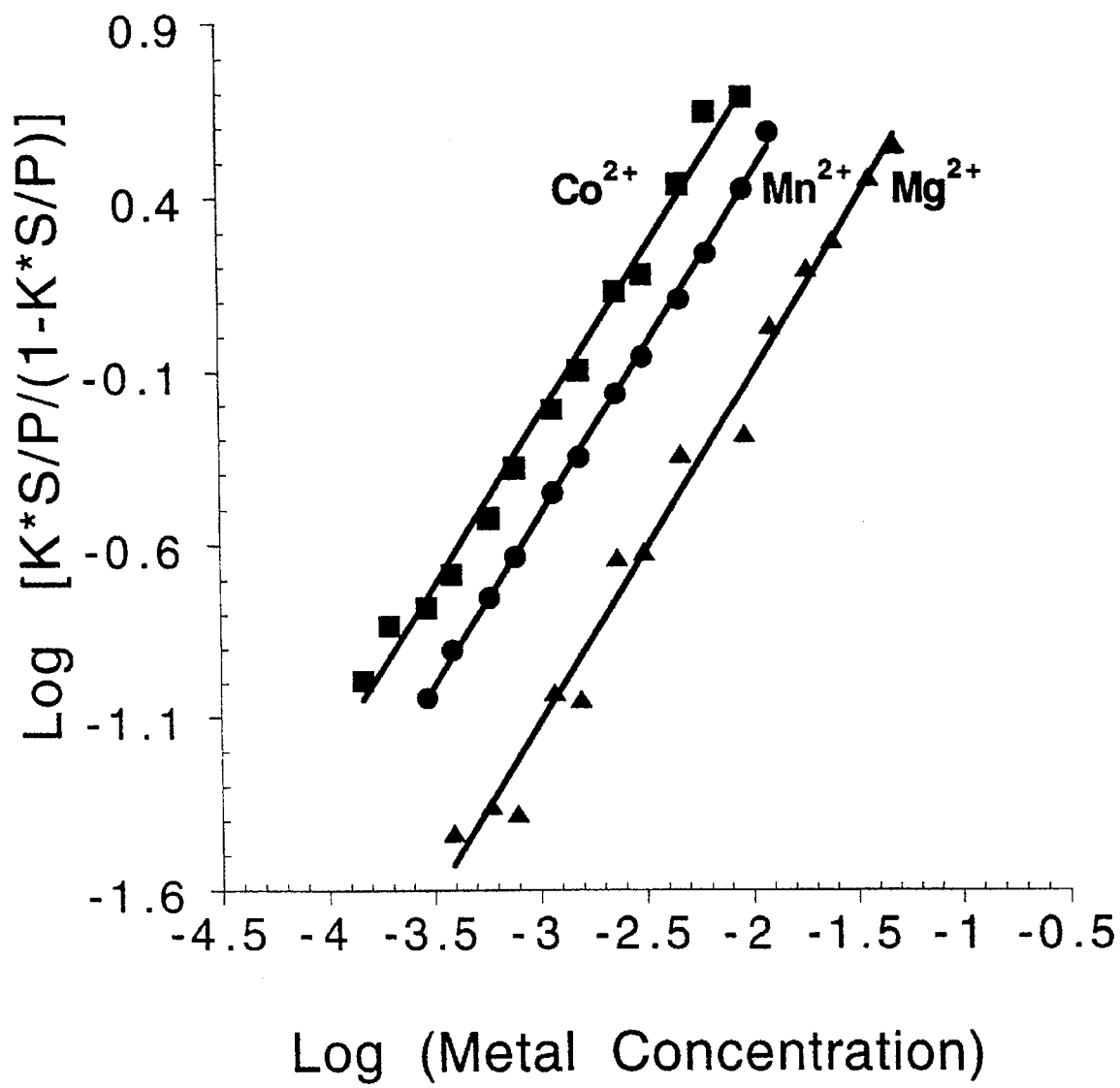
FIG. 3 shows Hill plots to determine the number of metals ions bound per ribozyme in the ligation reaction. All three plots give slopes of 1, suggesting that there is either one metal ion coupled to the equilibrium, or multiple metal ions that bind non-cooperatively.
Figure 4:
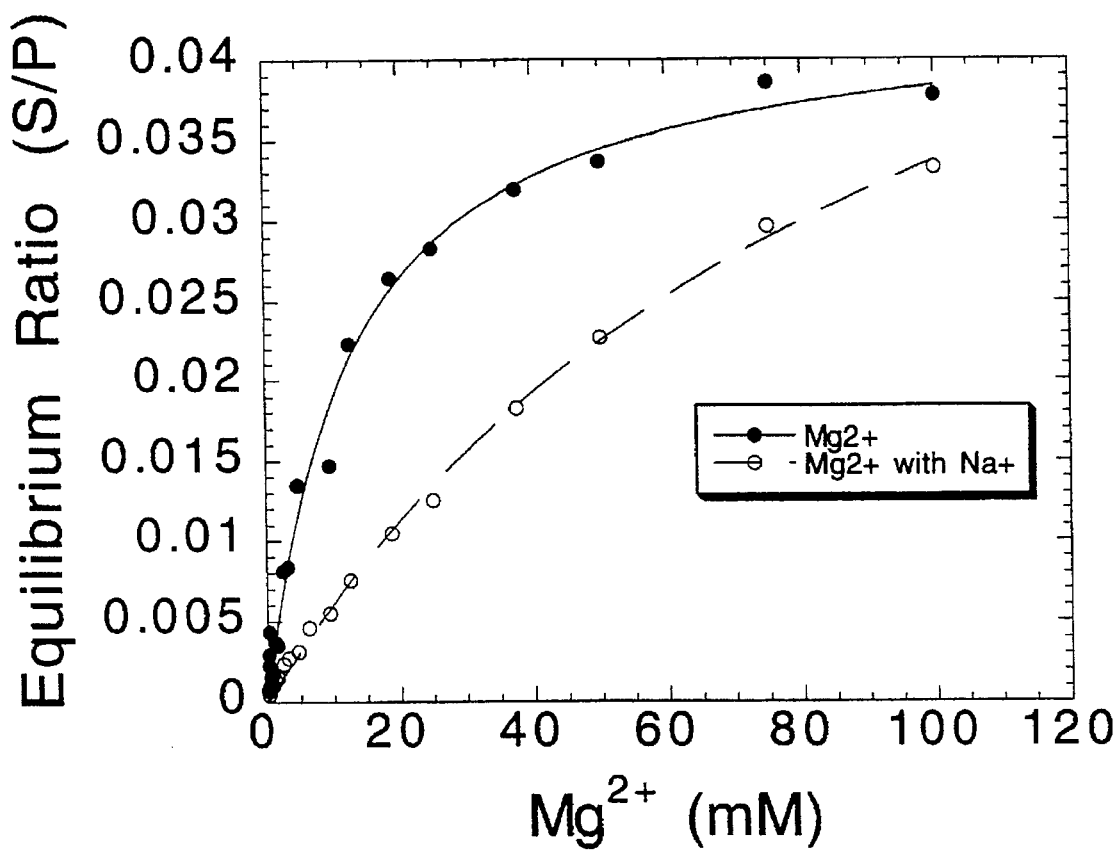
FIG. 4 is a plot of the metal ion dependence of S/P showing that it is not simply an ionic strength effect since compensation with sodium ions does not change the general form of the hyperbolic curves (although the curve is shifted to the right in the presence of $Na^+$). The concentration of NaCl was varied to keep the ionic strength of the reaction mixture constant.

Referring to FIG. 3, Hill-type plots of the S/P vs. metal data give slopes of 1 (noncooperative binding or single metal ion binding, i.e., one metal ion per hammerhead). FIG. 4 shows that the metal ion dependence of S/P is not simply an ionic strength effect since compensation with sodium does not change the general form of the hyperbolic curves (although the curve is shifted to the right in the presence of $Na^+$). In addition, FIG. 5 shows that when S/P is measured as a function of temperature in the presence of three metal ions low temperature provides ligation. The entropies and enthalpies of the reactions are very metal ion dependent and indicate that S/P is not an intrinsic property of the RNA alone.

Phosphorothioate linkages (in both, Sp and Rp diastereomeric forms) can be introduced at the cleavage/ligation site of a hammerhead ribozyme (Dahm, S. C. and Uhlenbeck, O. C (1991) *Biochemistry* 30, 9464–9469; Koizumi, M. and Ohtsuka, E. (1991) *Biochemistry* 30, 5145–5150). One of these substitutions is likely to enhance ligation efficiency based on different affinities of metal ions to phosphorothioates. Other equivalent alternations in chemical structure can be made to further enhance ligation efficiency of a hammerhead ribozyme.

Selection of Hammerhead Ribozymes

As described by Berzal-Herranz et al., supra, selection of ligation active hammerhead ribozymes can be performed now that ligation enhancing conditions are known. In addition, ribozymes having the noted modified thiophosphate group can be used, e.g., in conjunction with such ligation enhancing environmental conditions. Specifically, referring to FIG. 2 of Berzal-Herranz et al, an in vitro selection scheme is summarized. The hammerhead ribozyme is synthesized with a substrate attached. When the internal substrate is cleaved, its 3' end becomes available for ligation onto a trans-substrate. The FIG. 6 shows the two steps after the cleavage of the internal substrate. These steps are binding and cleavage of a trans-substrate (the trans-substrate has to compete with the remaining half of the internal substrate) and displacement of one of the two trans-substrate cleavage products followed by ligation of the other trans-substrate cleavage product onto the bound portion of the internal substrate. The hammerhead substrate-binding arms can be adjusted to ensure that one portion of the cleaved target dissociates quickly (by making that arm short) while the other portion stays bound (by increasing the length of that binding arm) The selection strategy is completely described in this paper and can now be used to select ligation efficient hammerhead ribozymes.

Further specific examples are provided in FIGS. 6 and 7 in which the hexagonal moiety represents a selected domain as described in Berzal-Herranz et al. The selected domain can be nucleic acids, peptides, etc. This domain can be selected in the procedure described to enhance for ligation efficiency. Once an intermolecular cleavage reaction has occurred, this will be followed by ligation to yield a chimeric RNA which can be amplified. In one example, hybridization to the 3' target fragment can be designed such that dissociation occurs after cleavage, for example, by using a short stem III in a hammerhead ribozyme.

Referring to FIG. 7, the ligation reaction may be carried out in vitro using the above-specified conditions or equivalent conditions; the ligation reaction is preferably performed on molecules that are cleaved either in vitro or in vivo or as determined by either standard hammerhead cleavage reactions, other nuclease digestion reactions, chemical modification reactions or RNAseH digestion reaction or equivalent reactions. That is, the ligation efficiency is tested on known sites of accessibility to other types of agents. The cleaved RNA target should have a free 5' hydroxyl group but may have any sequence as indicated by the ends in the Figure. Each end is independently any nucleotide or non-nucleotide but preferably is a ribonucleotide or deoxyribonucleotide. Amplified chimeric RNA that self-cleaves during the standard transcription reaction described Berzal-Herranz et al. to yield a ligation competent molecule is useful for further cycles of selection. In addition, the efficiently ligating hammerhead ribozyme can be made complementary to either 3' or 5' cleaved fragment of the target molecule (FIG. 7 shows the 5' configuration). If the hammerhead is made complementary to the 3' fragment, that fragment should have a UH>P terminus (H>P—A, U or C ribonucleotide with a 2', 3' cyclic phosphate at its 3' terminus). That is, a terminus expected following RNA cleavage by the hammerhead ribozyme.

Other embodiments are within the following claims.

We claim:

1. A method for ligation of an enzymatic nucleic acid molecule having a hammerhead motif to an RNA molecule, comprising the steps of:

contacting in a reaction mixture said enzymatic nucleic acid molecule with said RNA molecule wherein said reaction mixture contains an ion selected from the group consisting of: cobalt, manganese, cadmium, zinc, copper, and nickel ions, in which ligation is enhanced at least two fold over that observed in a medium containing only $Mg^{2+}$ as a divalent cation at 20° C.

2. The method of claim 1, wherein said RNA molecule is an oligonucleotide having between 5 and 100 nucleotides, or greater than 10,000 nucleotides.

3. The method of claim 1, wherein said conditions enhance ligation at least 5-fold.

4. The method of claim 1, wherein said conditions enhance ligation at least 10-fold.

5. The method of claim 1, wherein said conditions enhance ligation at least 30-fold.

6. The method of claim 1, wherein said conditions comprise cobalt or manganese ions.

7. The method of claim 1, wherein said conditions comprise a temperature between 2° C. and 15° C.

8. The method of claim 7, wherein said conditions comprise a temperature between 2° C. and 5° C.

9. The method of claim 1, wherein said conditions cause at least 10% ligation of said enzymatic nucleic acid molecule to said RNA molecule.

10. The method of claim 1, wherein said conditions cause between 20–50% ligation of said enzymatic nucleic acid molecule to said RNA molecule.

11. A method for generating efficient ligation of a hammerhead ribozyme to a target RNA comprising ligation condition comprising manganese or cobalt ions at a temperature below 20° C.

12. A method for selection of a potential target site for cleavage by a hammerhead ribozyme comprising the step of determining a site accessible for ligation sites for said hammerhead ribozyme in said target, wherein said determining is by use of the method of claim 1.

13. The method of claim 12 wherein said selection is in vitro.

14. A method for selection of a ligation efficient enzymatic nucleic acid molecule with a hammerhead motif, comprising the steps of selecting for hammerhead molecules able to ligate to separate RNA molecules under ligation enhancing conditions wherein said ligation enhancing conditions comprise an ion selected from the group consisting of: cobalt, manganese, cadmium, zinc, copper, and nickel ions.

15. The method of claim 14, wherein said conditions comprise cobalt or manganese ions at a temperature below 20° C.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 59
        ( B ) TYPE: nucleic acid
        ( C ) STRANDEDNESS: single
        ( D ) TOPOLOGY: linear ( i i ) SEQUENCE DESCRIPTION: SEQ ID NO: 1:

```
GUCGUCGCGC  GAUGACCUGA  UGAGGCCGAA  AGGCCGAAAC  GUUCUCGCGA        50

GAGAACGUC                                                         59
```

( 2 ) INFORMATION FOR SEQ ID NO: 2:

( i ) SEQUENCE CHARACTERISTICS:
        ( A ) LENGTH: 59
        ( B ) TYPE: nucleic acid
        ( C ) STRANDEDNESS: single
        ( D ) TOPOLOGY: linear ( i i ) SEQUENCE DESCRIPTION: SEQ ID NO: 2:

```
GUCGUCGCGC  GAUGACCUGA  UGAGGCCGAA  AGGCCGAAAC  GUUCUCGCGA        50

GAGAACGUC                                                         59
```

( 2 ) INFORMATION FOR SEQ ID NO: 3:

( i ) SEQUENCE CHARACTERISTICS:
        ( A ) LENGTH: 43
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for an
        base, or a non-nucleotide.

( i i ) SEQUENCE DESCRIPTION: SEQ ID NO: 3:

```
NNNNNNNNHU  NNNNNUHNNN  NNAAAGCGAG  UAGUCNNNNN  NNN              43
```

( 2 ) INFORMATION FOR SEQ ID NO: 4:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
        base, or a non-nucleotide.

( i i ) SEQUENCE DESCRIPTION: SEQ ID NO: 4:

```
NNNNNNNNHU  AAAGCGAGUA  GUCNNNNNNN  N                            31
```

( 2 ) INFORMATION FOR SEQ ID NO: 5:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear (ix) FEATURE:
  (D) OTHER INFORMATION: The letter "N" stands for any base, or a non-nucleotide.

(ii) SEQUENCE DESCRIPTION: SEQ ID NO: 5:

NNNNNNNNHU AAAGCGAGUA GUCNNNNNNN N　　　　31